(12) United States Patent
Van den Engh

(10) Patent No.: US 7,923,252 B2
(45) Date of Patent: Apr. 12, 2011

(54) DROPLET FORMATION SYSTEMS FOR FLOW CYTOMETERS

(75) Inventor: Ger Van den Engh, Seattle, WA (US)

(73) Assignee: University of Washington, Seattle, WA (US)

( * ) Notice: Subject to any disclaimer, the term of this patent is extended or adjusted under 35 U.S.C. 154(b) by 1779 days.

(21) Appl. No.: 11/069,529

(22) Filed: Feb. 28, 2005

(65) Prior Publication Data

US 2005/0153458 A1 Jul. 14, 2005

Related U.S. Application Data

(60) Continuation of application No. 09/689,585, filed on Oct. 12, 2000, now Pat. No. 6,861,265, which is a division of application No. 08/627,963, filed on Apr. 16, 1996, now Pat. No. 6,133,044, which is a continuation of application No. 08/323,270, filed on Oct. 14, 1994, now abandoned.

(51) Int. Cl.
  *G01N 21/85* (2006.01)
  *G01N 33/48* (2006.01)
(52) U.S. Cl. .......................................... 436/63
(58) Field of Classification Search ............... 436/63
  See application file for complete search history.

(56) References Cited

U.S. PATENT DOCUMENTS

| | | | |
|---|---|---|---|
| 3,299,354 A | 1/1967 | Hogg | 324/71 |
| 3,661,460 A | 5/1972 | Elking et al. | 356/36 |
| 3,761,941 A | 9/1973 | Robertson | 346/1 |
| 3,810,010 A | 5/1974 | Thom | 324/71 |
| 3,826,364 A | 7/1974 | Bonner | 209/3 |
| 3,960,449 A | 6/1976 | Carleton et al. | 356/103 |
| 3,963,606 A | 6/1976 | Hogg | 209/3 |
| 3,973,196 A | 8/1976 | Hogg | 324/71 |
| 4,014,611 A | 3/1977 | Simpson et al. | 356/72 |
| 4,070,617 A | 1/1978 | Kachel et al. | 324/71 |
| 4,162,282 A | 7/1979 | Fulwyler et al. | 264/9 |
| 4,230,558 A | 10/1980 | Fulwyler | 209/3.1 |

(Continued)

FOREIGN PATENT DOCUMENTS

EP   025 296   3/1981

(Continued)

OTHER PUBLICATIONS

Gottlinger, et al., "Operation of a Flow Cytometer", Flow Cytometry and Cell Sorting, 1992, pp. 7-23.

(Continued)

*Primary Examiner* — Jan M Ludlow
(74) *Attorney, Agent, or Firm* — Sterne, Kessler, Goldstein & Fox PLLC

(57) ABSTRACT

A droplet forming flow cytometer system (1) allows high speed processing without the need for high oscillator drive powers through the inclusion of an oscillator or piezoelectric crystal (10) within the nozzle volume (3) and directly coupled to the sheath fluid. The nozzle container (27) continuously converges so as to amplify unidirectional oscillations (11) which are transmitted as pressure waves through the nozzle volume (3) to the nozzle exit so as to form droplets from the fluid jet. A variation in substance concentration is achieved through a movable substance introduction port (9) which is positioned within a convergence zone (32) to vary the relative concentration of substance to sheath fluid while still maintaining optimal laminar flow conditions. This variation may be automatically controlled through a sensor and controller configuration.

7 Claims, 5 Drawing Sheets

U.S. PATENT DOCUMENTS

| | | | |
|---|---|---|---|
| 4,302,166 A | 11/1981 | Fulwyler et al. | 425/6 |
| 4,317,520 A | 3/1982 | Lombardo et al. | 209/3.1 |
| 4,318,480 A | 3/1982 | Lombardo et al. | 209/3.1 |
| 4,318,481 A | 3/1982 | Lombardo et al. | 209/3.1 |
| 4,318,482 A | 3/1982 | Barry et al. | 209/3.1 |
| 4,325,483 A | 4/1982 | Lombardo et al. | 209/3.1 |
| 4,361,400 A | 11/1982 | Gray et al. | 356/23 |
| 4,395,676 A | 7/1983 | Hollinger et al. | 324/71.4 |
| 4,487,320 A | 12/1984 | Auer | 209/3.1 |
| 4,515,274 A | 5/1985 | Hollinger | 209/3.1 |
| 4,538,733 A | 9/1985 | Hoffman | 209/3.1 |
| 4,631,483 A | 12/1986 | Proni et al. | 324/71.4 |
| 4,660,971 A * | 4/1987 | Sage et al. | 356/39 |
| 4,673,288 A | 6/1987 | Thomas et al. | 356/72 |
| 4,691,829 A | 9/1987 | Auer | 209/3.1 |
| 4,818,103 A | 4/1989 | Thomas et al. | 356/72 |
| 4,845,025 A | 7/1989 | Lary et al. | 435/2 |
| 4,981,580 A | 1/1991 | Auer | 209/3.1 |
| 4,983,038 A | 1/1991 | Ohki et al. | 356/246 |
| 5,005,981 A | 4/1991 | Schulte et al. | 366/219 |
| 5,007,732 A | 4/1991 | Ohki et al. | 356/73 |
| 5,079,959 A | 1/1992 | Miyake et al. | 73/864.85 |
| 5,144,224 A | 9/1992 | Larsen | 327/71.4 |
| 5,159,397 A | 10/1992 | Kosaka et al. | 356/73 |
| 5,159,403 A | 10/1992 | Kosaka | 356/243 |
| 5,167,926 A | 12/1992 | Kimura et al. | 422/67 |
| 5,182,617 A | 1/1993 | Yoneyama et al. | 356/440 |
| 5,199,576 A | 4/1993 | Corio | 209/564 |
| 5,215,376 A | 6/1993 | Schulte et al. | 366/348 |
| 5,247,339 A | 9/1993 | Ogino | 356/73 |
| 5,259,593 A | 11/1993 | Orme et al. | 266/78 |
| 5,260,764 A | 11/1993 | Fukuds et al. | 356/73 |
| 5,359,907 A | 11/1994 | Baker et al. | 73/865.5 |
| 5,370,842 A | 12/1994 | Miyazaki et al. | 422/82.06 |
| 5,412,466 A | 5/1995 | Ogino | 356/246 |
| 5,819,948 A | 10/1998 | Van den Engh | 209/158 |
| 6,133,044 A | 10/2000 | Van den Engh | |
| 6,263,745 B1 | 7/2001 | Buchanan et al. | |
| 6,861,265 B1 | 3/2005 | den Engh | |
| 2006/0141628 A1* | 6/2006 | Evans | 436/63 |

FOREIGN PATENT DOCUMENTS

| | | |
|---|---|---|
| EP | 160 201 A2 | 11/1985 |
| EP | 160 201 AO | 11/1985 |
| EP | 468 100 A1 | 1/1992 |
| JP | 61-139747 | 6/1986 |
| JP | 61-159135 | 7/1986 |
| JP | 02-024525 | 1/1990 |
| JP | 04-126066 | 4/1992 |
| JP | 04-126081 | 4/1992 |
| SU | 1 056 008 | 11/1983 |
| WO | WO 96/12171 | 4/1996 |

OTHER PUBLICATIONS

Melamed, et al., Flow Cytometry and Sorting (1st Edition), 1979, pp. 3-9.

Pinkel, et al., "Flow Chambers and Sample Handling", Flow Cytometry: Instrumentation and Data Analysis. 1985, pp. 77-126.

U.S. Appl. No. 08/323,270, entitled "High Speed Flow Cytometer Droplet Formation System", filed Oct. 14, 1994.

U.S. Appl. No. 09/689,585, entitled "Flow Cytometer Droplet Formation System", filed Oct. 12, 2000.

U.S. Appl. No. 08/627,963, entitled "High Speed Flow Cytometer Droplet Formation System", filed Apr. 15, 1996.

Van Dilla, et al., "Overview of Flow Cytometry: Instrumentation and Data Analysis", Flow Cytometry: Instrumentation and Data Analysis, 1985, pp. 1-8.

Australian Patent Application No. 398582/95; Office Action dated Dec. 22, 1997.

Australian Patent Application No. 398582/95; Letters Patent No. 698929 issued Feb. 25, 1999.

European Regional Patent Application No. 95 937 480.2, Office Action dated Jan. 14, 2002.

European Regional Patent Application No. 95 937 480.2, Notice of Oral Proceedings Jul. 18, 2002.

European Regional Patent Application No. 95 937 480.2, Notice of Grant dated Jun. 12, 2003.

European Regional Patent Application No. 95 937 480.2, Patent Certificate No. 0786078 dated Jan. 7, 2004.

* cited by examiner

DROPLET FORMATION SYSTEMS FOR FLOW CYTOMETERS

This application is a continuation of U.S. application Ser. No. 09/689,585 filed Oct. 12, 2000, now U.S. Pat. No. 6,861, 265 to be issued on Mar. 1, 2005, which is a divisional of U.S. application Ser. No. 08/627,963, filed Apr. 16, 1996, now U.S. Pat. No. 6,133,044 issued on Oct. 17, 2000, which is a continuation of U.S. application Ser. No. 08/323,270 filed Oct. 14, 1994, now abandoned; each of these are hereby incorporated by reference herein.

I. BACKGROUND OF THE INVENTION

Generally this invention relates to droplet flow cytometers such as are used for the analysis and sorting of substances contained within separate droplets. Specifically, the invention relates to aspects of such systems which act to form regular droplets after exit from a nozzle orifice.

Droplet flow cytometers have been in clinical and research use for many years. Basically, the systems act to position small amounts of a substance within individual droplets of a sheath fluid. These droplets can be made uniform by utilizing an oscillator which emits a predominant frequency. These oscillations are usually applied to the nozzle container. Since droplet flow cytometry is heavily utilized in both research and clinical environments, such systems have been the subject of much refinement. One of the facets of these systems which has been particularly challenging, however, is the aspect of controlling the drop formation. As to this aspect it has not only been difficult to practically achieve processing rates of much more than 40 kilohertz, it has also been difficult to deal with the incidents of using relatively high power to drive the oscillators involved.

It should be noted that each of the challenges faced in the field of droplet formation for flow cytometers is largely unique to that field. Even seemingly similar fields such as those involving channel-type flow cytometers are not very analogous as they do not face such problems. Their operation as continuous flow devices rather than droplet formation devices makes much of the understandings available in that field inapplicable to the challenges and problems faced in flow cytometry droplet formation systems.

To some degree the challenges for droplet formation may be the result of the fact that although drop formation has been modeled with significant theoretical detail, in practice it still remains a somewhat empirical subject. While on one level exhaustive mathematical predictions are possible, in practice these predictions can be greatly tempered—and are often revised—by the fact that materials limitations, inherent substance variations, and the like contribute heavily to the end result. A number of "advances" in this field have even proved to be either unnecessary or unworkable in practice.

The level of oscillation energy required in order to achieve uniform droplet formation has, prior to the present invention, been very subject to empirical constraints. This power (often expressed as a voltage amplitude applied to a piezoelectric crystal oscillator) has previously been in the ten volt range. Unfortunately, this relatively high voltage not only results in a need for more robust circuitry, but it also has the undesirable practical consequence of resulting in undesirable electromagnetic emissions. These emissions can impact the sensitivity of the flow cytometer or other nearby equipment. Further, as the desire for higher processing frequencies is pursued, this problem is compounded. Although these problems have been know for years, prior to the present invention it has apparently been an accepted attitude that in order to achieve higher frequencies, still higher oscillation energies are a physical requirement. This invention proves this expectation to be untrue. An example of the extremes to which this rational had been applied is shown in U.S. Pat. No. 4,361,400 to Gray where droplet formation frequencies in the range of 300 to 800 kilohertz had been achieved. This design had required an oscillator powered by approximately 80 volts. The apparent physical requirement of higher powers in order to achieve higher droplet frequencies may have been one reason that most practical droplet flow cytometers operated only in the range of 10 to 50 kHz. The present invention shows that such a relationship is not a physical requirement and, in fact, shows that droplet formation speeds in the 100-200 kHz range are actually possible with only millivolts of power applied to an oscillator.

Yet another problem practically encountered in this field was the challenge of resonances existing within the nozzle assembly. Again, this appears to have simply been accepted as a necessary incident of workable systems and may have resulted in an attitude among those having ordinary skill in the art that it was not practical to vary frequency without unacceptable changes in the performance of the entire system. There also seems to have been some confusion as to the appropriate way to apply the droplet forming oscillations. U.S. Pat. No. 4,302,166 shows that the oscillations are applied to the nozzle container perpendicular to the fluid flow, whereas, U.S. Pat. No. 4,361,400 suggests applying the oscillations to the nozzle container parallel to the lines of flow. In fact, the present invention discloses that each of these systems are suboptimal in that they may even act to generate the resonances and variations in frequency response of the nozzle system.

An even more paradoxical situation exists with respect to the problem of maintaining laminar flow within the nozzle system of a droplet flow cytometer. Although those having ordinary skill in this field have known for years that maintaining laminar flow was desirable, until the present invention, practical systems utilizing replacement tips have not been optimally designed so as to achieve the goal of truly laminar flow. For instance, U.S. Pat. No. 4,361,400 as well as the 1992 publication by Springer Laboratory entitled "Flow Cytometry And Cell Sorting", each show replaceable nozzle tip designs in which laminar flow is disrupted at the junction between the nozzle body and the nozzle tip. Again, such designs seem to present almost a paradox in that they obviously are not optimum from perspective of a goal which has long been known as those having ordinary skill in the art. The present invention not only recognizes this goal but also demonstrates that a solution has been readily available.

Yet another problem encountered in this field is the need to vary parameters to optimize actual conditions encountered in processing. Again theory and practice did not mix well. While systems were usually designed for optimum conditions, in actual usage such conditions rarely existed. Thus, as U.S. Pat. No. 4,070,617 recognized, designs which allow variation of the substance output velocity within the sheath fluid were desirable. Although such systems permitted some variation, it was recognized that such variations necessarily made conditions within the flow cytometer suboptimal for the simple reason that there is a very definite physical relationship between the sheath substance and drop parameters which must be maintained. Since these parameters are well known to those having ordinary skill in the art (as also indicated in U.S. Pat. No. 4,302,166), the variations required in practice appear to have been accepted as a necessary evil. To some extent, the resulting reduced resolution appears to have been accepted without question. Again, the present invention realizes that approaches which moved conditions away from optimal were not a necessary incident of adapting to conditions practically encountered; it shows that solutions which allow for variation and yet maintain optimal flow conditions are possible.

As explained, most of the foregoing problems had long been recognized by those having ordinary skill in the art. Solutions, however, had either been perceived as unlikely or not been recognized even though the implementing elements had long been available. This may also have been due to the fact that those having ordinary skill in the art may not have fully appreciated the nature of the problem or may have been due to an actual misunderstanding of the physical mechanisms involved. These appear to have included the misunderstanding that actually moving the nozzle was the proper way to induce the droplet forming oscillations and the simple failure to realize that it was possible to coordinate the desire for replaceable nozzle tips with the desire for laminar flow within the flow cytometer nozzle assembly. Similarly, those skilled in the art had long attempted to achieve higher frequency systems which were practically implementable and had attempted to achieve variations which would to the largest extent possible maintain optimal conditions. Their attempts often led them away from the technical directions taken by the present invention and may even have resulted in the achievements of the present invention being considered an unexpected result of the approach taken.

II. SUMMARY OF THE INVENTION

The present invention involves a number of improvements which are applicable to a flow cytometer droplet system. These improvements each offer independent advantages and may be combined synergistically to produce a great increase in the performance of droplet flow cytometers. The preferred embodiment involves a piezoelectric oscillator contained within the sheath fluid above a continuously converging nozzle container. This nozzle container acts to amplify the oscillations which are directly and directionally coupled to the sheath fluid. Further, the location of the substance introduction tube may be adjusted within a convergence zone so as to vary the rate at which the substance is introduced relative to the rate at which the sheath fluid is introduced to maintain optimal conditions. In addition, a replaceable nozzle tip is fit within an edge insert and sealed on its outer surface so as to maintain laminar flow and enhance the amplification of the oscillation throughout the converging nozzle body. As a result of the combination of these various features, the present invention not only achieves practical processing at frequencies of many multiples of typical prior art devices, but it also achieves these processing rates at oscillation powers which are several orders of magnitude less than those typically utilized.

Accordingly, one of the objects of the invention is to provide for a low power system which allows high processing rates. In keeping with this object, one goal is to achieve direct coupling of the oscillations to the sheath fluid and thus minimize any losses associated with material interfaces. In keeping with this object, another goal is to provide for a system which actually amplifies the oscillations so as to produce acceptable fluid variations at the nozzle tip.

Yet another object of the invention is to minimize the impacts of resonance frequencies within the nozzle system. In keeping with this object, a goal is to directionally couple the oscillations to the sheath fluid. It is also a goal to isolate the oscillations from imparting upon the sheath fluid in more than the desired direction.

A further goal of the invention is to provide for a system which allows for the maintenance of laminar flow within the entire nozzle assembly while allowing for both replaceable nozzle tips and for internal variations. The present invention achieves the first object by providing a design which avoids the unnecessary impacts of a seal on the flow condition within the nozzle container. The second object is achieved by providing a system which varies the location at which a substance is introduced while still maintaining optimal, laminar conditions.

Still another object of the invention is to provide for a practically implementable system. In keeping with this object, one goal is to provide a system which can be easily cleaned and for which components can be easily replaced. A goal is also providing a design which can be relatively easily and inexpensively manufactured.

Naturally, further objects of the invention are disclosed throughout other areas of the specification and claims.

III. BRIEF DESCRIPTION OF THE DRAWINGS

IV. DETAILED DESCRIPTION OF THE PREFERRED EMBODIMENT

Figure 1:
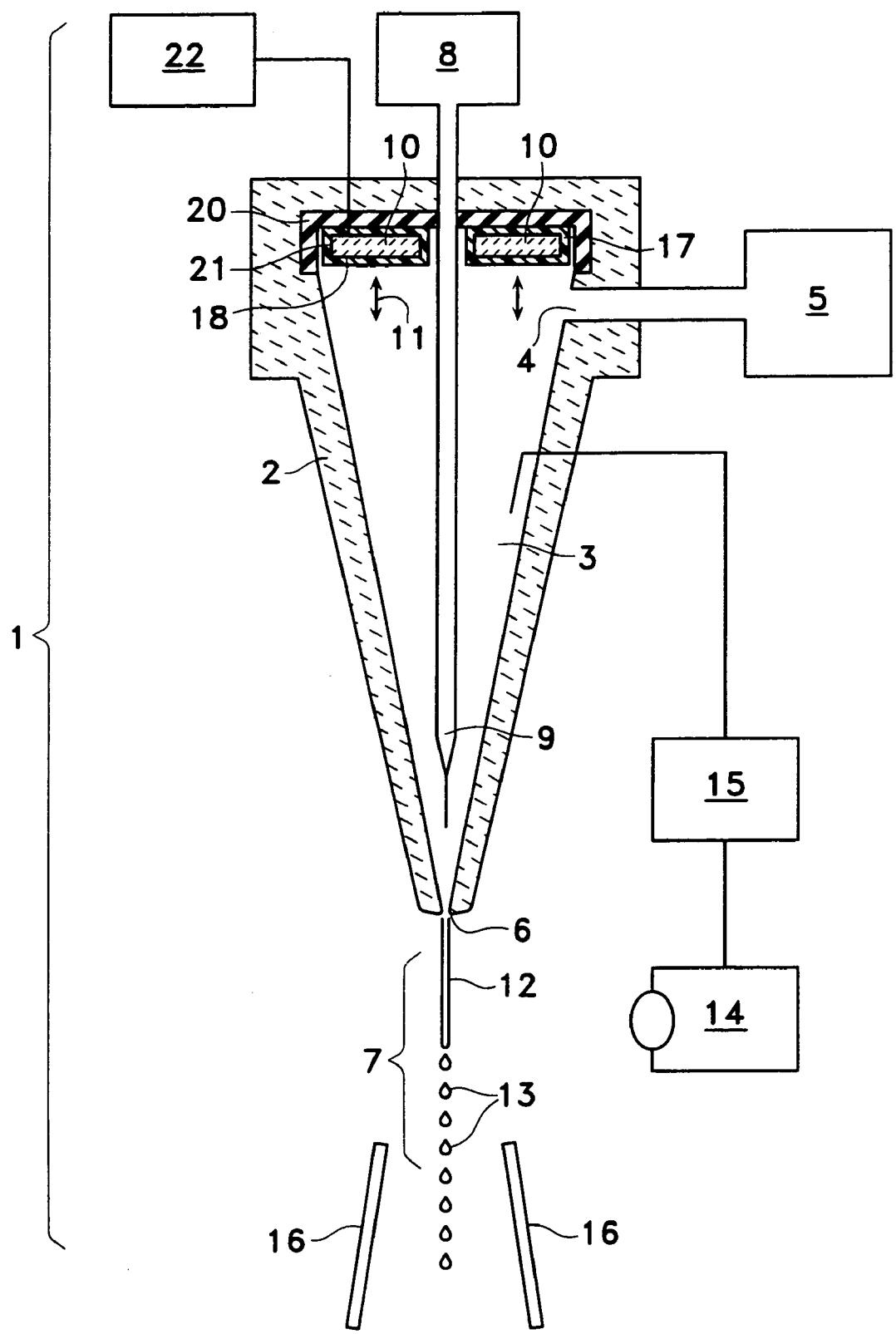
FIG. 1 is a schematic cross sectional view of an embodiment of the invention showing the various features combined.

As mentioned, the present invention involves an improved flow cytometer droplet nozzle system which incorporates a variety of features. As shown in FIG. 1, the flow cytometer system (1) involves nozzle container (2) which establishes nozzle volume (3). Nozzle volume (3) is supplied a liquid by sheath fluid port (4) which acts to introduce a sheath fluid from some sheath reservoir (5). During operation, the sheath fluid flows through nozzle container (2) and out nozzle exit (6) into free fall area (7).

Since the sheath fluid is typically an unreactive substance such as a saline fluid and is an analytically transparent, it has introduced within it some desirable substance such as cells or parts of cells or other items. This substance is maintained in substance reservoir (8) and is introduced to nozzle volume (3) through substance introduction port (9). Through hydrodynamic focusing, the substance flows and is separated into single cell units within the sheath fluid and exits at nozzle exit (6).

In order to form regular droplets, the preferred embodiment utilizes a piezoelectric crystal (10) to cause oscillations (11) within the sheath fluid. These oscillations are transmitted as pressure variations through to nozzle exit (6) and act to allow jet (12) to form regular droplets (13) through the action of surface tension. These processes are well understood and are further explained in a number of references including the 1992 reference entitled *"Flow Cytometry and Cell Sorting"* by A. Radbruch (© Springer-Verlag Berlin Heidelberg) and the 1985 reference entitled *"Flow Cytometry: Instrumentation and Data Analysis"* edited by Marvin A. Van Dilla, et al. (© Academic Press Inc. (London) Ltd.) each of which are incorporated by reference.

As shown in FIG. 1, one of the features of the preferred embodiment is the location of piezoelectric crystal (10) within nozzle volume 3. By this feature the oscillator acts to initiate oscillations (11) within the nozzle volume. The oscillator thus may be directly coupled to the sheath fluid. These oscillations are transmitted through the sheath fluid as it flows out nozzle exit (6) and forms droplets (13) below nozzle (6) in freefall area (7). Naturally, although shown to be directly below it is possible that the nozzle assembly could be oriented on its side or in some other relationships and so droplets (13) might form at some other location and yet still be characterized as "below" nozzle tip (6) since they will form in the direction that jet (12) is emitted from nozzle exit (6).

As is well understood, by allowing sheath fluid and the substance to exit from nozzle container (2), cells or cell fragments may be isolated in singular fashion within separate droplets (13) for analysis by sensor (14) which feeds its information to analysis equipment (15). Analysis equipment (15) may provide the necessary data or may act to further process droplets (13) through some equipment such as an electrode in nozzle volume (3) in combination with sorting electrostatic field equipment (16) as is well known in the art. When electrostatic potentials are applied, they may be applied differentially to each droplet based upon the delay in droplet formation. This analysis equipment (15) may also include a separate laser which induces fluorescence and the like in specific cells to allow further sensing and facilitate conducting analysis as well.

As may be easily understood from FIG. 1, this type of flow cytometer, a droplet flow cytometer, operates quite differently from a channel forming flow cytometer. In channel-type flow cytometers, oscillators and the theories involved are not relevant as no freefall or droplet formation is required. Further, while the nozzle exit orifice is approximately 50 to 150 microns in diameter in droplet forming flow cytometers, in channel-type flow cytometers, the orifice can be much larger —on the order of 1000 microns. This causes extremely different conditions and has resulted in the two fields being treated somewhat differently by those involved.

Another feature of the invention is how the oscillator couples to actually cause the formation of droplets (13). As shown in FIG. 1, the oscillator is in this embodiment piezoelectric crystal (10). While, naturally, a variety of different devices could be used in order to achieve oscillation (11), by using piezoelectric crystal (10) a host of different frequencies and powers are possible. It should be understood, however, that while the use of some piezoelectric crystal is usually the preferred technique, the invention should not be considered as limited to that type of oscillator as its teachings can be broadly applied.

As shown in FIG. 1, piezoelectric crystal (10) is configured as a ring-shaped crystal which occupies most of the top end of nozzle container (2). This ring is mounted directly to nozzle container (2) in a manner so as to be situated within nozzle volume (3). It need not vibrate the nozzle container and, indeed is designed to avoid it. Its oscillations (11) may also be made to occur generally in a direction parallel to the central axis of nozzle container (2) as shown. Further, these oscillations (11) are essentially coupled to the sheath fluid, not to the nozzle container. Thus, rather than taking the directions suggested by some of the prior art involving moving the actual nozzle container, the present invention acts directly upon the sheath fluid to cause pressure variations within the sheath fluid. These pressure variations move down nozzle volume (3) and may actually be amplified by the shape of nozzle container (2) so as to cause surface tensions variations in jet (12) as it emerges from nozzle exit (6). These variations act to pinch off jet (12) and thus form droplets (13). Since the sheath fluid is not substantially compressible, these pressure variations may pass relatively unattenuated and in fact may be amplified through nozzle volume (3) to achieve the desired droplet formation effect. While others may have considered the desire to coupling directly to the sheath fluid, they failed to recognize ways to do this and did not recognize that they could have positioned the oscillator within the sheath fluid for most efficient coupling.

Both the direct coupling of oscillations (11) to the sheath fluid and the directional nature of the oscillations (11) contribute to the invention's ability to achieve droplet formation at power levels which are several orders of magnitude less than those of the prior art. As may be understood from FIG. 1, piezoelectric crystal (10) may directly transfer the vast majority of its energy to the sheath fluid. To further enhance the transfer of the majority of the energy into the sheath fluid (rather than the nozzle as often suggested by the prior art), the invention may also incorporate the designing of massive nozzle container elements so as to minimize the transfer of energy through these elements. As may be easily understood, by positioning the oscillator within the sheath fluid, frequency dependencies and resonances which are caused by the vibration of the entire nozzle container can be greatly reduced. Thus, contrary to the teachings of the prior art which suggested vibrating the entire nozzle container, the present invention can specifically avoid such vibrations. This acts to avoid resonance frequencies as might occur through vibrations perpendicular to the lines of flow which may be inevitable whenever the entire nozzle assembly is vibrated. Contrary to those teachings which have suggested mounting the entire nozzle assembly on a flexible membrane so as to allow the entire nozzle assembly to move, the present invention relies not on movement of nozzle container (2) but rather on pressure waves within the sheath fluid in nozzle volume (3). This aspect greatly reduces the amount of power necessary to cause droplet formation and greatly reduces the appearance of resonance frequencies which occur as a result of the entire vibration of nozzle container (2) among other aspects.

Figure 2:
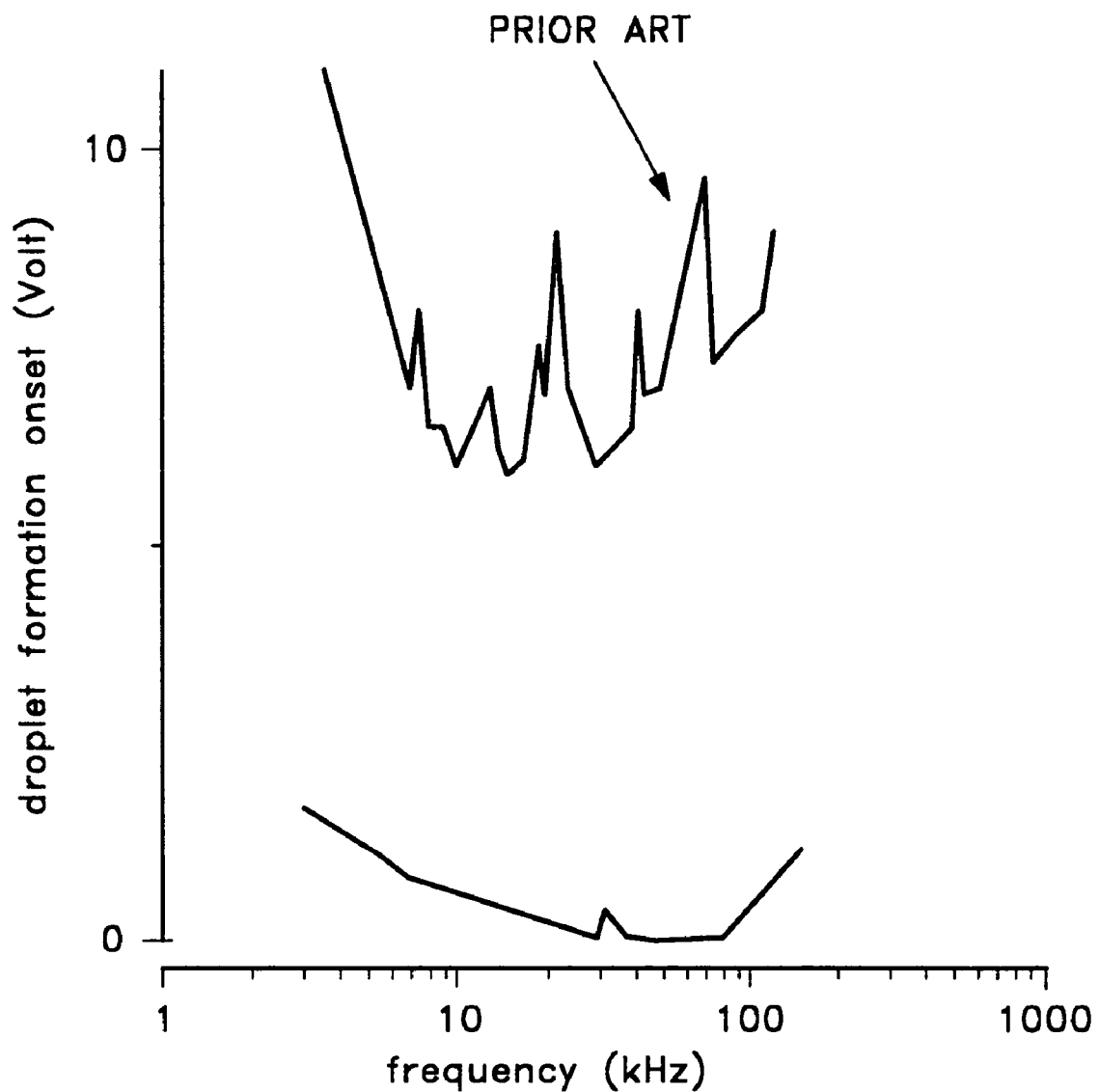
FIG. 2 is a plot of the droplet onset energy of prior art designs compared to that of the present invention.

Referring to FIG. 2, the dramatic impact of these reductions can be understood. FIG. 2 shows a conceptual plot of the rough energy of droplet formation onset versus frequency anticipated for the present invention. As shown in FIG. 2, the energy (expressed in terms of volts applied to a given piezoelectric crystal) is reduced by orders of magnitude. This reduction has been demonstrated for a number of frequencies. As shown in FIG. 2, the prior art which typically operated in the 10 volt range now only requires ten millivolts or so.

In addition, as shown in FIG. 2, it can be seen that the prior art was also subject to a great number of resonance frequency variations (shown by the peaks and valleys in the plot of the prior art). These peaks and valleys were to a large extent caused not only by the amount of power required but also by designs which were based upon movement of the entire nozzle assembly rather than merely pressure waves within the nozzle assembly. In sharp contrast to the prior art characteristic conceptually shown in FIG. 2, the present invention not only achieves droplet formation with dramatically lower voltages but it also achieves these levels over a relatively large frequency range with very small resonance variations compared to those of the prior art. These relative plots are believed to represent significant differences in result between prior art designs and those of the present invention. While naturally variations will occur due to the particular nozzle designs ultimately chosen, it is believed that through the teachings of the present invention these dramatic variations should be practically achievable in many cases.

Referring again to FIG. 1, it can be seen that besides merely positioning the oscillator within nozzle volume (3), the embodiment also is designed to minimize the number of material interfaces through which the oscillations must pass before being imparted upon the sheath fluid. While, naturally, it would be possible to position piezoelectric crystal (10) directly exposed to the sheath fluid, for contamination and other reasons, the preferred embodiment allows for the inclusion of protective coating (17) over piezoelectric crystal (10). This protective coating (17) may actually be some type of epoxy or other coating which has no tendency to interfere either with the sheath material or the oscillations (11) of piezoelectric crystal (10). Again, contrary to the teachings of the prior art which involve numerous material interfaces between the oscillator and the sheath fluid, the present invention minimizes the number of material interfaces through which oscillations (11) must pass. Since any change in material can cause reflection and energy losses, the preferred design allows for only one interface material such as protective coating (17). Thus, only one interface material exists between oscillator surface (18) and the sheath fluid. By positioning piezoelectric crystal (10) within nozzle volume (3) not only can the interface material be limited to the simple epoxy coating mentioned, but also, the oscillator surface (18) can be positioned so as to face directly to the sheath fluid.

Figure 3:
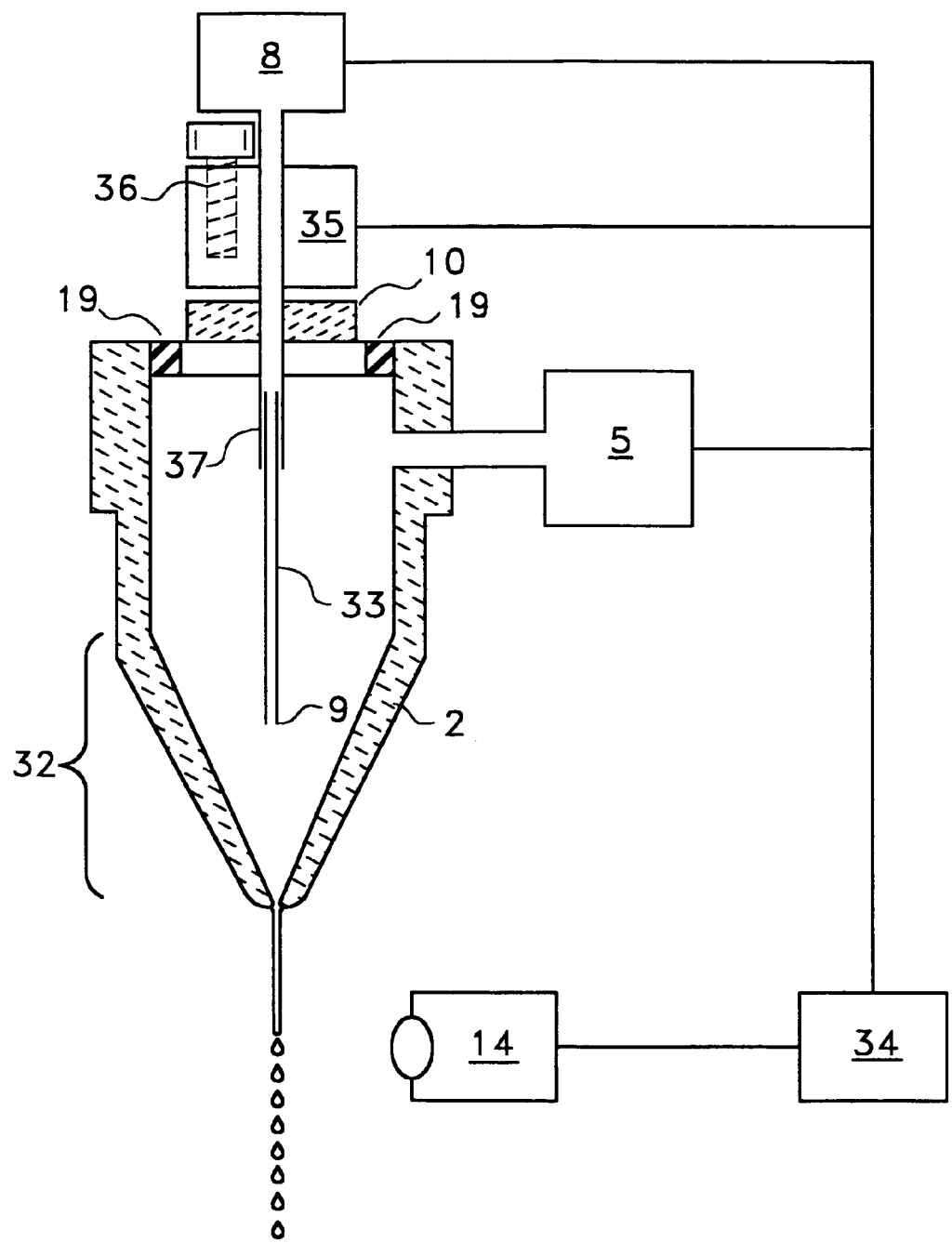
FIG. 3 is a schematic cross sectional view of an alternative design showing the automatic substance adjustment feature and a directionally coupled, external oscillator.

As mentioned, another aspect which helps the invention achieve its extraordinary reduction in oscillation drive power is the fact that the oscillator is directionally coupled to the sheath fluid. In order to avoid resonances and energy transmissions in other than the desired direction, the present invention recognizes that unidirectional coupling is desirable. In order to achieve this, as shown in FIG. 1 the embodiment provides for positioning piezoelectric crystal (10) so that it is detached from the sides of nozzle container (2). Since all piezoelectric crystals act in a manner so as to conserve volume during oscillations, this avoids coupling the inherent perpendicular oscillations to nozzle container (2). Again, through this recognition, the invention can achieve a uniform pressure wave within the sheath fluid. Since oscillator surface (18) is oriented perpendicular to the primary flow direction, the oscillations (11) are coupled substantially only as a flow direction deemed to be primary, whether the average flow direction, a specific location's flow direction, or even the direction at the nozzle exit (6). This allows for the oscillations to be unidirectionally applied to the sheath fluid and also aids in the reduction of resonance frequencies. As shown in FIGS. 1 and 3, this unidirectional coupling can be achieved through the inclusion of a directional isolator (19). As shown in FIG. 3, directional isolator (19) may be a separate element such as a rubber or other material which does not transmit frequencies of the predominant oscillation frequency. As shown in FIG. 1, the directional isolator (19) may actually be spacer (20). Spacer (20) may be a separate element or, as shown in FIG. 1, may be an integral portion of the top or cap of nozzle container (2) so as to simply act to space oscillator side (21) away from nozzle container (2). The unidirectional coupling of oscillations (11) to the sheath fluid may be enhanced by making oscillator surface (13) planar as shown in FIG. 1 and by making it cover most of the top surface area. The oscillator is thus established substantially throughout a perpendicular cross sectional area (perpendicular to the primary flow direction) and will cause oscillations throughout it. Thus the ring shaped crystal design coordinates the desire to maximize the surface area of oscillator surface (18) with the unidirectional desire by making it match the typically circular cross section of nozzle container (2). Naturally other shapes can also be used. Further, the coupling, shown in FIG. 1 and in FIG. 3 as the portion of the top section of the nozzle container (2) may also be planar and may also be coupled along only one plane. These each contribute to making the main oscillation area cause only one direction of oscillation as can be easily understood.

To further enhance the reduction in oscillation power achievable through the present invention, nozzle container 2 is also designed as a continuously converging nozzle container. This acts to not only maintain laminar flow throughout nozzle volume (3), but also to effectively amplify oscillations (11) as they travel in pressure waves through the sheath fluids from piezoelectric crystal (10) to nozzle exit (6). As may be understood from FIG. 1, by continuously converging it is not meant that nozzle volume (3) must constantly or uniformly converge throughout its length, rather, it need only converge at all locations. Thus, nozzle volume (3) has a largest cross-sectional area located at or near its top and has continuously diminishing cross-sectional areas along its length through to nozzle exit (6).

Having a continuously converging nozzle container also helps in maintaining laminar flow up to nozzle exit (6). In this regard nozzle exit (6) should be understood to exist not only at the actual end location of the orifice but more accurately at the point at which there is a significant increase in the pressure gradient so as to make changes in the angle of convergence less important. Unlike the teachings of the prior art which frequently involve straight cylindrical sections within nozzle container (2), this aspect of the invention specifically avoids such possibilities. This is somewhat surprising and may be treated with skepticism by those of ordinary skill in the art because traditional theories provide that once laminar flow is established such flow should continue in most applications when the nozzle container does not expand sharply. In contrast, this aspect of the invention suggests otherwise. While these traditional laminar flow theories may be appropriate in some instances, the continuous convergence of the sheath fluid appears desirable in most droplet flow cytometers. To some extent this may be due to the fact that the required acceleration of the sheath fluid and pressure, and the resulting increase in the friction of the sheath fluid against nozzle container (2), each make a constant convergence desirable to avoid nonlaminar flow results. Basically it has been empirically found that through a continuously converging nozzle container optimal conditions for maintaining laminar flow can be created.

In addition to the aspect of maintaining laminar flow, the continuously converging nozzle container can provide amplification of the oscillations (11). Similar to horn and other designs, the continuous convergence combines with the principals of conservation of energy so that the amplitude of the oscillations actually increases as it passes from piezoelectric crystal (10) to nozzle exit (6). This amplification may be maximized not only by positioning the oscillator at or near the largest cross-sectional area but also by making oscillator surface (18) to have an area substantially as large as the largest cross-sectional area. In this regard by "substantially" it is meant that the oscillator should be as large as practically possible after consideration of the typical desire to introduce substance through the center axis of nozzle volume (3) as well as this invention's unique desire to maintain oscillator side (21) spaced apart from nozzle container (2). The amplification may also be enhanced by providing for continuous convergence from sheath fluid port (4) through to nozzle exit (6). As mentioned earlier, each of the foregoing aspects also contribute to the present invention's extraordinary reduction in input power requirements.

To create oscillations (11), piezoelectric crystal (10) is powered through an alternating voltage source (22) as those skilled in the art can easily understand. Through the teachings of the present invention, alternating voltage source (22) may be configured to stimulate the oscillator with the voltage amplitude of less than 100 millivolts and thus represents orders of magnitude of reduction in the typical voltage applied to piezoelectric crystals in such systems. This voltage may be greater than 10 millivolts or so as that was a representative level at which droplet formation seems to occur. It should be understood, however, that this limitation should not be taken as a lower limit since the teachings of this invention may become refined and alternative designs may be developed which result in further reduction in power.

Figure 4:
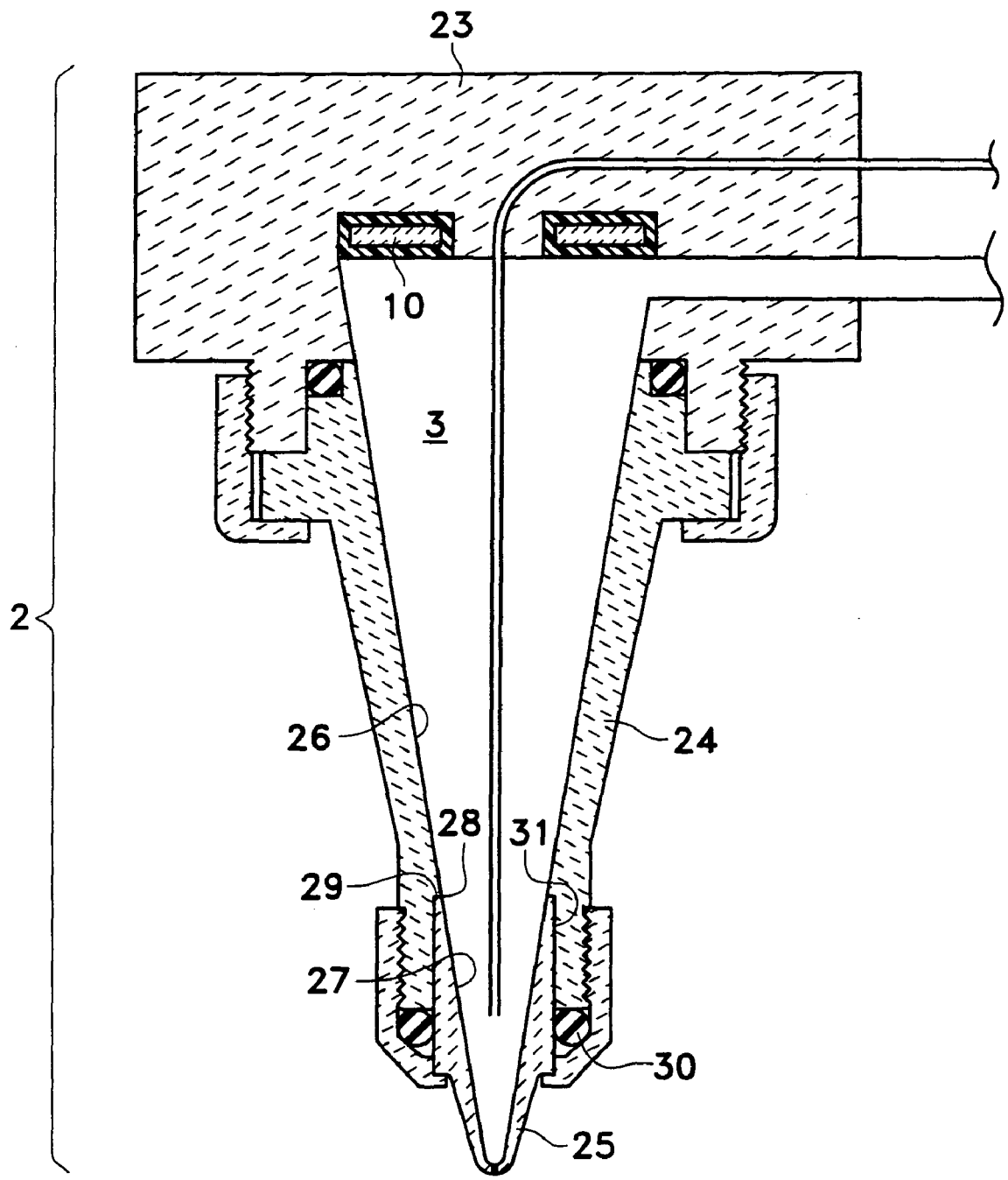
FIG. 4 is a cross sectional view of a replaceable tip design according to one embodiment of the invention.

Yet another independent feature of the present invention is its design to allow the nozzle section to be easily replaced or cleaned while permitting laminar flow. Referring to FIG. 4, it can be seen that the entire nozzle container (2) may be made of several components. Nozzle container (2) may consist of cap section (23) to which piezoelectric crystal (10) may be attached. Cap section (23) may be attached in some sealing fashion or may even be integral to nozzle body (24) as shown in FIG. 1. Similarly, nozzle body (24) may be sealingly attached to nozzle tip (25). Each of these seals may consist of O-rings as but one example of the types of seals shown in FIG. 4. Nozzle tip (25) may be a ceramic fabricated item which includes an exit situated at its tip. This exit may actually be an orifice made through techniques known by those skilled in the art (such as the use of tungsten wire and the like) so as to create a small orifice of about 50 to 150 microns in diameter.

Figure 5:
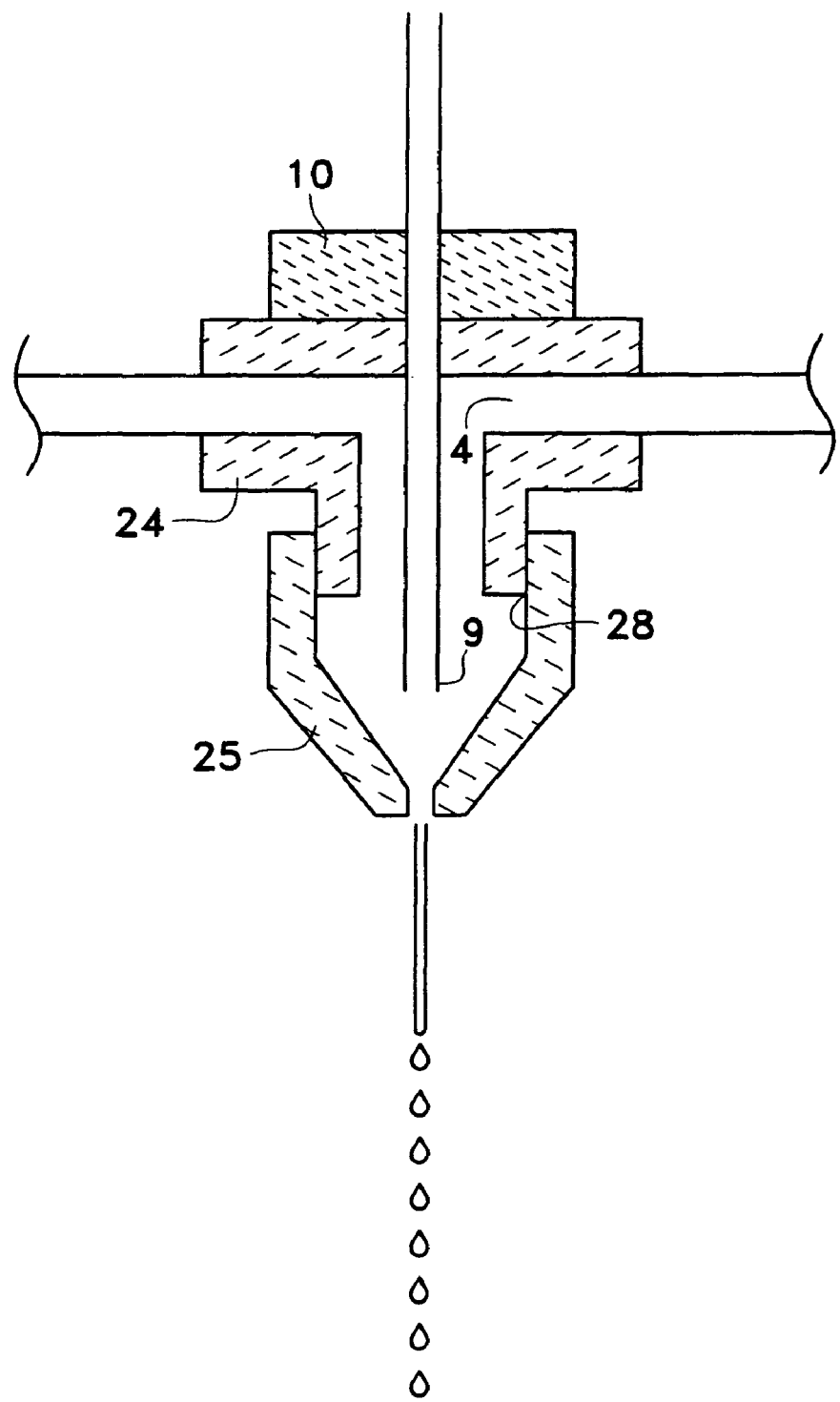
FIG. 5 is a cross sectional view of a prior art replaceable nozzle tip design.

Unlike the designs shown in the prior art such as those shown in FIG. 5, nozzle tip (25) need not be sealed to nozzle body (24) on its inner surface. Instead, the nozzle body inner surface (26) joins smoothly with the nozzle tip inner surface (27) at tip joint (28). This smooth transition is to the degree necessary to maintain laminar flow in the particular application. It can be achieved through the inclusion of edge insert (29) within nozzle body (24) so as to allow nozzle tip (25) to be inserted into nozzle body (24). In this fashion seal (30) can be positioned so as to contact the outer surface (31) of nozzle tip (25) and thus avoid any adverse impacts on laminar flow within nozzle volume (3). By locating seal (30) off of inner surface (27) of nozzle tip (25), the seal can be kept away from areas which are important to laminar flow. As may be understood, a great variety of designs may be accomplished to achieve this goal. Importantly, it should be understood that inner surface (27) of nozzle tip (25) is defined merely with respect to its function, namely, the surface which contacts and directs the flow of sheath fluid of nozzle volume (3). Further, the definition of "smooth" is also relatively defined as those transitions which do not significantly interrupt laminar flow and thus do not degrade the performance of the flow cytometer. It should also be understood that the seal between any two components such as the seal between nozzle body (24) and nozzle tip (25) may be direct or indirect through the use of intervening materials or components.

Yet another independent aspect of the invention is the aspect of being able to adjust the location at which the substance is introduced. As mentioned earlier, those skilled in the art have long recognized the need to achieve variations in the entire process to accommodate variations in conditions practically experienced. As shown in FIG. 3, the present invention affords the ability to vary the rate at which substance is introduced without disrupting laminar flow and the like. This is achieved through positioning substance introduction port (9) within convergence zone (32) as may be easily understood and by varying the location of substance introduction port (9) within is convergence zone (32). As shown, substance introduction port (9) may move along the primary flow direction to maintain an optimal relationship to the flow of the sheath fluid. Through this technique, the relative concentrations of the substance introduced and the sheath fluid can be varied. This can act to avoid the resolution drop and the like which the prior art appeared to consider unavoidable as they adapted to changing conditions.

Further, since it may be desirable to maintain equal velocities at substance introduction port (9), and since substance tube (33) may be moved, it is possible to include a controller (34) which receives signals from some type of sensor (14) and which may act to control a movement mechanism (35) and thus automatically adjust the location of substance introduction port (9) within nozzle container (2). Further, controller (34) may act to additionally control the pressure of substance reservoir (8) and sheath reservoir (5) for automatic correlation of the various factors based upon location or other parameters sensed. Since the theoretical relationship between these factors is well known for optimal conditions and since the programming or wiring of such a design could be easily achieved by those skilled in the art, a variety of designs may be implemented to achieve this goal. Given the great variety of flow cytometer systems possible, it should be understood that a great variety of sensed values may be used ranging from concentration of the substance contained within substance reservoir (8), to the actual location of substance introduction port (9), to the pressure of the various sheath fluid or substance fluids, to some other property of the substance sensed by sensor (14). Each of these—or any combination of them and other factors—may be adjusted automatically to achieve desired relationships or to simply optimize results without regard to the actual predicted values. Naturally, in keeping with this broad concept it should be understood that sensor (14) may not be just one sensor but may in fact be a host of different sensors positioned at various locations depending upon the particular condition existing within the flow cytometer desired to be sensed. While, of course, the sensor (14) will only ascertain specific values, these values can indicate results which may be used to more appropriately adjust the location of the substance introduction port.

Similarly, a host of different designs for the location adjuster (shown in FIG. 3 as movement mechanism (35)) are possible. The location adjuster may also include some type of screw means (36), that is, some type of device which allows relatively continuous movement with fine adjustment. It may also include telescoping substance tube (37) (shown in FIG. 3 as potentially a redundant location adjuster for illustrative purposes only) or perhaps some type of slide design through the cap section. In applications in which the conditions remain relatively stable, a replacement substance tube of fixed length may also be provided. Thus, various substance tubes may be selected based upon the conditions encountered in that particular type of application. In this fashion, the limitation experienced by the prior art whereby variations in pressure were used but undesirably resulted in unequal fluid velocities at the location of substance introduction port (9) can be avoided. This affords an increase in the resolution.

The foregoing discussion and the claims which follow describe the preferred embodiment of the present invention. Particularly with respect to the claims and the broad concept discussed, it should be understood that changes may be made without departing from the essence of this patented invention. It is intended that changes are permissible to accommodate varying applications and will still fall within the scope of this patent. It is simply not practical to describe and claim all possible revisions nor is it practical to claim all combinations of the varying features. To the extent revisions utilize the essence of the present invention, each would naturally fall within the breath or protection encompassed by this path. This is particularly true for the present invention since its basic concepts and understandings are fundamental in nature and can be broadly applied. It is also particularly true since the present invention involves a number of potentially independent features which may be combined in synergistic ways for particular applications.

I claim:

1. A method of creating a droplet from a jet of a flow cytometer comprising:
    introducing a flow of sheath fluid into a nozzle, said sheath fluid having a primary flow direction through the nozzle;
    converging said sheath fluid in a convergence zone in the nozzle;
    introducing a flow of a substance at a location within said sheath fluid in said convergence zone;
    adjusting the location along the primary flow direction at which said substance is introduced within said convergence zone;
    allowing said sheath fluid to exit from said nozzle; and
    forming at least one droplet from said sheath fluid after allowing said sheath fluid to exit from said nozzle.

2. A method of creating a droplet from a jet of a flow cytometer according to claim 1 wherein said adjusting the location at which said substance is introduced within said convergence zone comprises establishing a desired concentration of said substance relative to said sheath fluid.

3. A method of creating a droplet from a jet of a flow cytometer according to claim 1 or 2 wherein said adjusting the location at which said substance is introduced within said convergence zone comprises establishing laminar flow of said substance within said sheath fluid.

4. A method of creating a droplet from a jet of a flow cytometer according to claim 1 wherein said adjusting the location at which said substance is introduced within said convergence zone is automatic.

5. A method of creating a droplet from a jet of a flow cytometer according to claim 1 wherein said adjusting the location at which said substance is introduced within said convergence zone comprises:
    sensing values representative of conditions within said flow cytometer; and
    automatically moving said location based upon said sensed values.

6. A method of creating a droplet from a jet of a flow cytometer according to claim 5 wherein said conditions are at least one of the following: the pressure of said sheath fluid; the pressure of said substance; the location at which said droplet is formed; the rate at which droplet is determined to contain some of said substance; or a property of said substance.

7. A method of creating a droplet from a jet of a flow cytometer according to claim 1 wherein said substance is introduced through a substance tube and wherein said adjusting the location at which said substance is introduced within said convergence zone comprises replacing said substance tube.

* * * * *

UNITED STATES PATENT AND TRADEMARK OFFICE
CERTIFICATE OF CORRECTION

PATENT NO. : 7,923,252 B2
APPLICATION NO. : 11/069529
DATED : April 12, 2011
INVENTOR(S) : Ger Van den Engh Page 1 of 1

It is certified that error appears in the above-identified patent and that said Letters Patent is hereby corrected as shown below:

In the Specification

In column 1, above the subtitle "BACKGROUND OF THE INVENTION", insert the following subtitle and paragraph:

--STATEMENT REGARDING FEDERALLY-SPONSORED RESEARCH AND DEVELOPMENT

This invention was made with government support under DE-FG06-93ER-61662 awarded by Department of Energy. The government has certain rights in the invention.--

Signed and Sealed this
Eighteenth Day of February, 2014

Michelle K. Lee
*Deputy Director of the United States Patent and Trademark Office*